US006383751B1

(12) United States Patent
Barendse

(10) Patent No.: US 6,383,751 B1
(45) Date of Patent: May 7, 2002

(54) ASSESSING LIPID METABOLISM

(76) Inventor: William John Barendse, 37 Ghost Gum Street, Bellowrie, QLD 4070 (AU)

(*) Notice: Subject to any disclaimer, the term of this patent is extended or adjusted under 35 U.S.C. 154(b) by 0 days.

(21) Appl. No.: 09/530,479

(22) PCT Filed: Oct. 23, 1998

(86) PCT No.: PCT/AU98/00882

§ 371 Date: Jul. 18, 2000

§ 102(e) Date: Jul. 18, 2000

(87) PCT Pub. No.: WO99/23248

PCT Pub. Date: May 14, 1999

(30) Foreign Application Priority Data

Oct. 30, 1997 (AU) .............................. PP 0120

(51) Int. Cl.$^7$ .......................... C07H 21/04; C12Q 1/68
(52) U.S. Cl. ...................... 435/6; 536/23.1; 536/24.31; 536/24.3; 536/24.33
(58) Field of Search .............................. 435/6; 536/23.1, 536/24.31, 24.3, 24.33

(56) References Cited

U.S. PATENT DOCUMENTS

| 5,612,179 A | 3/1997 | Simons .......................... 435/6 |
| 5,614,364 A | 3/1997 | Tuggle et al. ................... 435/6 |

FOREIGN PATENT DOCUMENTS

| WO | WO 90/15815 | 12/1990 | .......... C07H/21/04 |
| WO | WO 92/13102 | 8/1992 | ............ C12Q/1/68 |

OTHER PUBLICATIONS

Ron et al. "Detection of individual loci affecting economic traits in the USA Holstein population with the aid of DNA microsatellites" Animal Genetics, vol. 27, E017, p. 105, 1996.*
Hansen et al. "Thyroid–specific and cAMP–dependent hypersensitive regions in thyroglobulin gene chromatin" Eur. J. Biochemistry, vol. 178, pp. 387–393, 1988.*
de Martynoff et al. EMBL Accession No. X05380, Nov. 1987.*
Lendent et al. EMBL Accession No. M358823, Aug. 1990.*
Y. Malthiery et al., 1987, "Primary structure of thyroglobulin deduced from the sequence of its 8448 base complementary DNA" *Eur. J. Biochem.* 165(3):491–498.
W. Barendse et al., 1997, "A medium density genetic linkage map of the bovine genome" *Mammalian Genome* 8:21–28.
A. Krust et al., 1989, "A third human retinoic acid receptor, hRAR–gamma" *Proc. Natl. Acad. Sci. USA* 86(14):5310–4.
J. Parma et al., 1987, "Structural organization of the 5' region of the thyroglobulin gene. Evidence for intron loss and "exonization" during evolution" *J. Mol. Biol.* 196(4):769–79.
G. de Martynoff et al., 1987, "Structural organization of the bovine thyroglobulin gene and its 5'–flanking region" *J. Biochem.* 164(3):591–9.
M. Georges et al., 1987, "Genetic variation of the bovine thyroglobulin gene studied at the DNA level" *Animal Genetics* 18:41–50.

* cited by examiner

*Primary Examiner*—Lisa B. Arthur
*Assistant Examiner*—Jeanine Goldberg
(74) *Attorney, Agent, or Firm*—Morgan & Finnegan, LLP

(57) ABSTRACT

This invention relates to methods and nucleic acid probes for assessing characteristics of lipid metabolism in animals, and in particular to methods of predicting fat levels in meat, milk, or other fat depots of animals. Thus the invention provides a method of assessing the fat metabolism characteristics of an animal, comprising the step of testing the animal for the presence or absence of one or more markers selected from the group consisting of: a) an allele of the 5' untranslated region of thyroglobulin; b) an allele of the DNA polymorphism CSSM34, associated with the gene encoding retinoic acid receptor gamma (RARG); and c) an allele of the DNA polymorphism ETH10, associated with 11-cis, 9-cis retinol dehydrogenase (RDH5). The invention is particularly applicable to predicting disposition of fat in muscle tissue, which produces the characteristic "marbling" of meat, and to assessment of milk fat content. The methods of the invention are useful in selection of animals, particularly cattle, for ability to produce high or low levels of milk fat content.

4 Claims, 2 Drawing Sheets

SEQUENCE LISTING

<160> NUMBER OF SEQ ID NOS: 18

<210> SEQ ID NO 1
<211> LENGTH: 23
<212> TYPE: DNA
<213> ORGANISM: Bos taurus

<400> SEQUENCE: 1 gggatgact acgagtatga ctg                                                23

<210> SEQ ID NO 2
<211> LENGTH: 23
<212> TYPE: DNA
<213> ORGANISM: Bos taurus

<400> SEQUENCE: 2
gtgaaaatct tgtggaggct gta                                               23

<210> SEQ ID NO 3
<211> LENGTH: 545
<212> TYPE: DNA
<213> ORGANISM: Bos taurus

<400> SEQUENCE: 3 gggatgact acgagtatga ctgtgcgtgt gtttggctta tctcatcaaa atctctacat         60
tctgtgttaa tggatctgcc tgttttgttc cctgccatat cctcatggcc tagaatagtg       120
tctgcttctc tatcagactc taaagaaaca ttgctaggag ggaaggaagg agcatggatg       180
aggagggagg gagcattgtg tttctctcac ggtgggcctg aacgtgtggc ccaccaagtt       240
gttaactttg gcctttaccc ctgaagatga attatgaagc cacaccccca gttcttcctt       300
ggtggctcag atggtcaaga atccacctgc aatgcgggag acctgggttt gatccctggg       360
ttgggaagat ccctggaga agggaatggc tacccactcc agtattctgg cctggagaat        420
cccatggaca gaggagcctg gcgggatgca gtccatgggg tctcagagag tcagatgtga       480
ctgagcgact ttcacacaca ctcgtccctg gttctgctcc cctacagcct ccacaagatt      540
ttcac                                                                   545

<210> SEQ ID NO 4
<211> LENGTH: 545
<212> TYPE: DNA
<213> ORGANISM: Bos taurus

<400> SEQUENCE: 4 gggatgact acgagtatga ctgtgcgtgt gtttggctta tctcatcaaa atctctacat         60
tctgtgttaa tggatctgcc tgttttgttc cctgccatat cctcatggcc tagaatagtg       120
tctgcttctc tatcagactc taaagaaaca ttgctaggag ggaaggaagg agcatggatg       180
aggagggagg gagcattgtg tttctctcac ggtgggcctg aacgtgtggc ccaccaagtt       240
gttaactttg gcctttaccc ctgaagatga attatgaagc cacaccccca gttcttcctt       300
ggtggctcag atggtcaaga atccacctgc aatgcgggag acctgggttt gatccctggg       360
ttgggaagat ccctggaga agggaatggc tacccactcc agtattctgg cctggagaat        420
cccatggaca gaggagcctg gcgggatgca gtccatgggg tctcagagag tcagatgtga       480
ctgagcgact ttcacacaca ctcgtccctg gttctgctcc cctacagcct ccacaagatt      540
ttcac                                                                   545

<210> SEQ ID NO 5
<211> LENGTH: 545
<212> TYPE: DNA
<213> ORGANISM: Bos taurus

<400> SEQUENCE: 5

| | | | | | |
|---|---|---|---|---|---|
| ggggatgact | acgagtatga | ctgtgcgtgt | gtttggctta | tctcatcaaa | atctctacat | 60 |
| tctgtgttaa | tggatctgcc | tgttttgttc | cctgccatat | cctcatggcc | tagaatagtg | 120 |
| tctgcttctc | tatcagactc | taaagaaaca | ttgctaggag | ggaaggaagg | agcatggatg | 180 |
| aggagggagg | gagcattgtg | tttctctcac | ggtgggcctg | aacgtgtggc | ccaccaagtt | 240 |
| gttaactttg | gcctttaccc | ctgaagatga | attatgaagc | cacaccccca | gttcttcctt | 300 |
| ggtggctcag | atggtcaaga | atccacctgc | aatgcgggag | acctgggttt | gatccctggg | 360 |
| ttgggaagat | tccctggaga | agggaatggc | tacccactcc | agtattctgg | cctggagaat | 420 |
| cccatggaca | gaggagcctg | gcgggatgca | gtccatgggg | tctcagagag | tcagatgtga | 480 |
| ctgagcgact | tcacacaca | ttcgtccctg | gttctgctcc | cctacagcct | ccacaagatt | 540 |
| ttcac | | | | | 545 |

<210> SEQ ID NO 6
<211> LENGTH: 24
<212> TYPE: DNA
<213> ORGANISM: Bos taurus

<400> SEQUENCE: 6
ccataactct gggactttc ctca                                          24

<210> SEQ ID NO 7
<211> LENGTH: 24
<212> TYPE: DNA
<213> ORGANISM: Bos taurus

<400> SEQUENCE: 7
atgttcagcc atctctcctt gtcc                                         24

<210> SEQ ID NO 8
<211> LENGTH: 931
<212> TYPE: DNA
<213> ORGANISM: Bos taurus

<400> SEQUENCE: 8

| | | | | | |
|---|---|---|---|---|---|
| tatgatacaa | ttcgagctcg | gtacctacat | gttcccaagg | atgctaatga | agatcactga | 60 |
| cctccggggc | atcagcacca | agggttagtc | gggagcaagc | ctccctctg | tcttctcgga | 120 |
| gctgccggtc | tcccaggtca | ggcagagaca | agagcaagtg | gggtataatc | aggcagcctg | 180 |
| cactcgcatc | ctcgctccgc | tgcatgctag | tgggaacact | tggtgcaaaa | tacctttcct | 240 |
| ttttgtacct | tgttttctg | tttgtgagga | tgaaacaagt | taacacacaa | caggcctaca | 300 |
| gctgtgctga | gttataaagt | tcagtgcctc | ctgccctgga | tggagcagat | gtttccacat | 360 |
| cacaggaagt | tgattggacg | cctggcacgc | ggtgtttgat | gaatgttagt | ctagtgataa | 420 |
| atgttattaa | gaacagccat | gggcttacgg | aggggtccag | tgtgtggctg | gaagtgggcg | 480 |
| ctgtgtgatc | ttggaggaga | cagcctgaaa | gaaagtgggc | agtggacttg | gcagagaaga | 540 |
| caggcagagt | tccaggcaga | ggagtgggcc | ccaggagctt | tacagtagaa | agagggagag | 600 |
| aaagaagcag | acagagataa | caggcctgtg | atgggagccc | cagagggcag | tcaagcagag | 660 |

-continued

```
ttagggaggc cgccgtaggt gctgtactca gcccctgaa ctcttgttct ccactgcagg      720
agcagaaagg gccattaccc tgaagatgga gattccaggc ccgatgcctc ccctgatccg      780
agaaatgctg gagaacccg aaatgtttga ggacgactcc tcgcagcctg gccctcaccc      840
caaggcctct agcgaggatg aggttcctgg ggatcctcta gagtcgacct gcaggcatgc     900
aagctaggca ctggccgtcg ttttacaaca a                                    931
```

<210> SEQ ID NO 9
<211> LENGTH: 23
<212> TYPE: DNA
<213> ORGANISM: Bos taurus

<400> SEQUENCE: 9

```
ccaaggatgc taatgaagat cac                                              23
```

<210> SEQ ID NO 10
<211> LENGTH: 23
<212> TYPE: DNA
<213> ORGANISM: Bos taurus

<400> SEQUENCE: 10

```
gactaacatt catcaaacac cgc                                              23
```

<210> SEQ ID NO 11
<211> LENGTH: 20
<212> TYPE: DNA
<213> ORGANISM: Bos taurus

<400> SEQUENCE: 11

```
ccgcgacaaa aactgtatca                                                  20
```

<210> SEQ ID NO 12
<211> LENGTH: 20
<212> TYPE: DNA
<213> ORGANISM: Bos taurus

<400> SEQUENCE: 12

```
ttgctgacct tggtgatgag                                                  20
```

<210> SEQ ID NO 13
<211> LENGTH: 20
<212> TYPE: DNA
<213> ORGANISM: Bos taurus

<400> SEQUENCE: 13

```
aatccgagag atgctggaga                                                  20
```

<210> SEQ ID NO 14
<211> LENGTH: 20
<212> TYPE: DNA
<213> ORGANISM: Bos taurus

<400> SEQUENCE: 14

```
cacccctaga aactttggca                                                  20
```

<210> SEQ ID NO 15
<211> LENGTH: 19
<212> TYPE: DNA
<213> ORGANISM: Bos taurus

<400> SEQUENCE: 15

```
atgccaagct gctctggtt                                                   19
```

```
<210> SEQ ID NO 16
<211> LENGTH: 24
<212> TYPE: DNA
<213> ORGANISM: Bos taurus

<400> SEQUENCE: 16
tgaagtgact gttttatgcc acac                                              24

<210> SEQ ID NO 17
<211> LENGTH: 22
<212> TYPE: DNA
<213> ORGANISM: Bos taurus

<400> SEQUENCE: 17
ttcaggactg gccctgctaa ca                                                22

<210> SEQ ID NO 18
<211> LENGTH: 23
<212> TYPE: DNA
<213> ORGANISM: Bos taurus

<400> SEQUENCE: 18
cctccagccc actttctctt ctc                                               23
```

ASSESSING LIPID METABOLISM

This application claims priority to International Patent Application PCT/AU98/00882 filed Oct. 23, 1998, and Australian Patent Application No. PP0120 filed Oct. 30, 1997.

This invention relates to methods and nucleic acid probes for assessing characteristics of lipid metabolism in animals, and in particular to methods of predicting fat levels in meat, milk, or other fat depots of animals. The invention is particularly applicable to predicting deposition of fat in muscular tissue, which produces the characteristic "marbling" of meat, and to assessment of milk fat content. The methods of the invention are useful in selection of animals, particularly cattle, for ability to produce or high levels of marbling in meat, and to produce high or low levels of milk fat content.

BACKGROUND OF THE INVENTION

The manner in which animals metabolise fat is of considerable economic significance in agriculture and animal husbandry. In some markets the high content of fat in meat, in the form of small fat deposits or "marbling", is regarded as highly desirable, and to induce heavy marbling of meat in cattle in particular the animals are grain fed for at least a short period prior to marketing and slaughter. In other markets a very lean meat is preferred. Similarly, a high fat content of milk is usually regarded as desirable. This can be particularly important if the milk is to be used for cheese production, and so these factors are important not only in cattle but also in sheep and goats. Recently generation of transgenic animals which secrete valuable proteins into their milk has been achieved, and in order to reduce the costs of purification of the desired protein a low content of fat in the milk is desirable.

Thus there is a need for methods by which the propensity of animals, particularly bovids and other ungulates, to deposit fat in muscle or to secrete fat into milk can be assessed.

Intramuscular or marbling fat is deposited in cattle between the fascicules of muscles, and usually develops when animals are fed a high calorie diet for a long time. The quantity of marbling fat is expressed either as a lipid concentration or as a standardised marbling score (eg. the Australian AUSMEAT standard). Unlike fat deposited in subcutaneous and renal depots, marbling fat is deposited continuously until relatively late in the development of the animal (Hood and Allen, 1973; Cianzio et al, 1985), and the amount of this fat is strongly correlated with the number of fat cells or adipocytes found in the muscle fascicules. Although some of the factors that are important in the differentiation of adipocytes are known (Ailhaud et al, 1992; Smas and Sul, 1995), the genetic factors that are involved in the difference between individuals in differentiation and development of the interfascicular adipocytes and deposition of fat were unknown, as were the genetic variants leading to a high or low marbling score.

To address this lack of information, we have obtained cattle samples from several breeds, the Angus, the Shorthorn and the Wagyu. These samples were readily differentiated due to their marbling score, with approximately half of the sample having a high marbling score and the other half of the sample having a low marbling score. We tested DNA markers from several regions of the bovine genome on the samples and the distribution of alleles was compared in the two groups.

Surprisingly, a significant association to marbling score was found with the anonymous DNA marker CSSM66. This marker had been assigned to bovine chromosome 14 (chr. 14) on the International Bovine Reference Family Panel (described in Barendse et al, 1997), with a location near the centromere. The gene for thyroglobulin (TG) is known to be located near this DNA marker (Barendse et al, 1997). TG is the molecular store for the thyroid hormones triiodothyronine and tetraiodothyronine, which have been implicated in the development of fat cells (Ailhaud et al, 1992; Darimont et al, 1993; Smas and Sul, 1995). TG has been sequenced in cattle (De Martynoff et al, 1987; Parma et al, 1987), and several DNA polymorphisms have been described previously (Georges et al, 1987). However, none of these polymorphisms is associated with fat or marbling.

We sought a polymorphism in the 5' untranslated region (5'UTR) of TG in cattle, since the transcriptional and translational regulation of genes is mediated by the 5'UTR (Ptashne, 1988; Beato, 1989; Kozak, 1991).

A novel polymorphism in the 5'UTR of TG was identified, and shown to be correlated with marbling. This polymorphism can be used as a test to select animals for marbling performance, either as breeding stock or as animals to be fed for particular markets. Other characteristics of fat, such as fat thickness in other fat depots as well as fat percentage of tissues, including milk, are expected to be predicted by this marker, since the iodothyronines affect the general differentiation of adipocytes and since the influence of the level of the thyroid hormones on milk fat percentage is well known (Folley and Malpress, 1948). It is also expected that fat percentage of other mammalian species will be predicted by variation in the 5'UTR of the TG of those species.

In addition, we have surprisingly found significant associations between marbling score and the hitherto anonymous DNA markers CSSM34 and ETH10 on chromosome 5. CSSM34 is associated with retinoic acid receptor gamma (RARG), which is a known factor in the growth and differentiation of adipocytes. ETH10 is associated with retinol dehydrogenase 5 (RDH5), which catalyzes the interconversion of retinol and retinoic acid, and the level of retinol in the serum is directly related to intramuscular fat levels. The thyroid and steroid hormones such as thyroxine, retinol, and estrogen bind to a family of nuclear receptors with a similar set of hormone response elements. These nuclear receptors, such as RARG, initiate the transcription of genes, and are important elements in the growth, differentiation and specification of tissues. These elements are linked together structurally by similarities at the DNA sequence level.

SUMMARY OF THE INVENTION

In its general aspect the invention provides a method of assessing the fat metabolism characteristics of an animal, comprising the step of testing the animal for the presence or absence of one or more markers selected from the group consisting of:

a) an allele of the 5' untranslated region of the gene encoding thyroglobulin;

b) an allele of the DNA polymorphism CSSM34, associated with the gene encoding retinoic acid receptor gamma (RARG); and c) an allele of the DNA polymorphism ETH10, associated with 11-cis, 9-cis retinol dehydrogenase (RDH5).

According to a first embodiment the invention provides a method of assessing the fat metabolism characteristics of an animal, comprising the step of testing the animal for the presence or absence of an allele of the 5' untranslated region of the gene encoding thyroglobulin.

Preferably the allele is allele 3, which indicates a high marbling score and/or high fat content of milk, or is allele 2, which indicates a low marbling score and/or low fat content in milk.

In a second embodiment the invention provides a method of identifying an animal with a high propensity for fat deposition in muscle (high marbling score), comprising the step of testing said animal for the presence or absence of allele 3 of the 5' untranslated region of the gene encoding thyroglobulin, and selecting those animals possessing the allele. Preferably the animal is also tested for the presence or absence of allele 2 of the 5' untranslated region of the gene encoding thyroglobulin, and those animals possessing allele 3 and not possessing allele 2 are selected. Most preferably the animal is homozygous for allele 3.

In a third embodiment, the invention provides a method of identifying an animal with a low propensity for fat deposition in muscle, comprising the step of testing the animal for the presence or absence of allele 2 of the 5' untranslated region of the gene encoding thyroglobulin, and selecting those animals having allele 2. Preferably the animal is also tested for allele 3, and those animals having allele 2 but not allele 3 are selected. Most preferably the animal is homozygous for allele 2.

According to a fourth embodiment the invention provides a method of identifying an animal with a high propensity for fat deposition in muscle (high marbling score), comprising the step of testing the animal for the presence or absence of an allele of the DNA polymorphism CSSM34 associated with the gene encoding retinoic acid receptor gamma (RARG).

Preferably the allele is allele 2, which indicates a high marbling score. Preferably the animal is also tested for other alleles at the CSSM34 DNA polymorphism. For high marbling scores the animal is most preferably homozygous for allele 2. Allele 2 is 102 base pairs (bp) of DNA long.

According to a fifth embodiment the invention provides a method of identifying an animal with a low propensity for fat deposition in muscle, comprising the step of testing the animal for the presence or absence of an allele of the DNA polymorphism CSSM34 associated with the gene encoding retinoic acid receptor gamma.

Preferably the allele is allele 6, which indicates a low marbling score. Preferably the animal is also tested for other alleles at the CSSM34 DNA polymorphism. For low marbling scores the animal is most preferably homozygous for allele 6. Allele 6 is 112 bp of DNA long.

According to a sixth embodiment the invention provides a method of identifying an animal with intermediate propensity for fat deposition in muscle (low marbling score), comprising the step of testing the animal for the presence or absence of an allele of the DNA polymorphism CSSM34 associated with the gene retinoic acid receptor gamma.

Preferably the allele is one or more of alleles 1, 3, 4, and 5 which indicates an intermediate marbling score. Preferably the animal is also tested for other alleles at the CSSM34 DNA polymorphism. The sizes of the alleles are given in Table 11. There is no special preference for genotype with these alleles. Other alleles may occur at CSSM34 with different lengths of DNA.

In a seventh embodiment, the invention provides a method of identifying an animal of, or derived from, the Wagyu cattle breed with a high propensity for fat deposition in muscle, comprising the step of testing the animal for the presence or absence of an allele of the ETH10 DNA marker. Preferably the allele is allele 5. Allele 5 is 223 bp long.

In an eighth embodiment, the invention provides a method of identifying an animal of, or derived from, the Wagyu cattle breed with a low propensity for fat deposition in muscle, comprising the step of testing the animal for the presence or absence of an allele of the ETH10 DNA marker. Preferably the allele is allele 2. Allele 2 is 217 bp long.

These embodiments of the invention are also applicable to the selection of animals for high or low fat content of milk respectively. The method is also useful for testing for fat levels in carcases.

According to a second aspect the invention provides a method of detecting one or more of the alleles of the invention in an animal, comprising the steps of:

a) obtaining a biological sample from the animal, b) extracting DNA from the sample, c) amplifying DNA from the relevant gene, and d) identifying alleles in the amplified DNA.

Preferably the DNA is either of the 5' untranslated region of thyroglobulin or of DNA segments near the retinoic acid receptor gamma; if the animal is of the Wagyu breed of cattle, the DNA segments are near the retinol dehydrogenase 5 gene.

Preferably the biological sample is blood, but other biological samples from which DNA can be amplified may be used. For example hair root samples, cheek scrapings, skin samples and the like may be used. Preferably for alleles of the 5' untranslated region of the thyroglobulin gene the region of DNA amplified includes a homopurine sequence and a copy of the monomeric dispersed repeat sequence. Preferably amplification is performed using polymerase chain reaction, but other DNA amplification methods such as ligase chain reaction are well known in the art, and may alternatively be used. Preferably the alleles are identified by polyacrylamide gel electrophoresis.

In a third aspect the invention provides oligonucleotide probes for amplification of the markers of the invention, selected from the group consisting of:

a) oligonucleotide probes for the 5' untranslated region of the thyroglobulin gene, having the sequences

```
TG5U2   5' ggg gat gac tac gag tat gac tg 3' (SEQ ID NO: 1)

TG5D1   5' gtg aaa atc ttg tgg agg ctg ta 3' (SEQ ID NO: 2)
``` b) oligonucleotide probes for amplication of the CSSM34 DNA marker, with the sequences

```
CSSM34U 5' cca taa ctc tgg gac ttt tcc tca 3' (SEQ ID NO. 6)

CSSM34D 5' atg ttc agc cat ctc tcc ttg tcc 3' (SEQ ID NO. 7)
``` c) oligonucleotide probes for amplication of fragments from the RARG gene in cattle, with sequences

```
RARGSJ1U 5' cca agg atg cta atg aag atc ac 3' (SEQ ID NO: 9)

RARGSJ1D 5' gac taa cat tca tca aac acc gc 3' (SEQ ID NO 10)

RARGE3U1 5' ccg cga caa aaa ctg tat ca 3'    (SEQ ID NO: 11)

RARGE3D1 5' ttg ctg acc ttg gtg atg ag 3'    (SEQ ID NO: 12)

RARGE8U2 5' aat ccg aga gat gct gga ga 3'    (SEQ ID NO: 13)

RARGE8D1 5' cac ccc tag aaa ctt tgg ca 3'    (SEQ ID NO: 14)
``` d) oligonucleotide probes for amplification of fragments from the RDH5 gene in cattle, with sequences

```
RDH5U  5' atg cca agc tgc tct ggt t 3'     (SEQ ID NO: 15)

RDH5D  5' tga agt gac tgt ttt atg cca cac 3' (SEQ ID NO: 16)
``` e) oligonucleotide probes for amplification of the ETH10 marker in Wagyu cattle, with sequences:

```
ETH10U 5' gtt cag gac tgg ccc tgc taa ca 3' (SEQ ID NO: 17)

ETH10D 5' cc tcc agc cca ctt tct ctt ctc 3' (SEQ ID NO: 18)
```

In a fourth aspect the invention identifies Yeast Artificial Chromosomes, which are positive by hybridization to the oligonucleotide primers for CSSM34U and CSSM34D as well as for RARGE8U2 and RARGE8D1. These are 77D3, 77E3, 71G8, 94B4 and 71E4.

In a sixth aspect the invention provides an isolated nucleic acid molecule encoding part of the bovine retinoic acid receptor gamma, having the sequence set out in SEQ ID NO: 8 as defined herein.

The methods of the invention may be used both for the selection of breeding animals and for the selection of unpedigreed animals for entry into feed lots. In the latter case, the methods of the invention are applicable to deciding the length of time which animals spend in feedlots, since a high marbling score is unlikely to be attained with animals which are homozygous for allele 2 of the 5' untranslated region of thyroglobulin or allele 6 of CSSM34, or a Wagyu animal with allele 2 of ETH10, even after long feedlot holding.

The methods of the invention are applicable to animals including but not limited to cattle and other bovids, including water buffalo and bison, to other ungulates, including sheep, goats and deer, and to pigs.

For the purposes of this specification it will be clearly understood that the word "comprising" means "including but not limited to", and that the word "comprises" has a corresponding meaning.

DETAILED DESCRIPTION OF THE INVENTION

Figure 1:
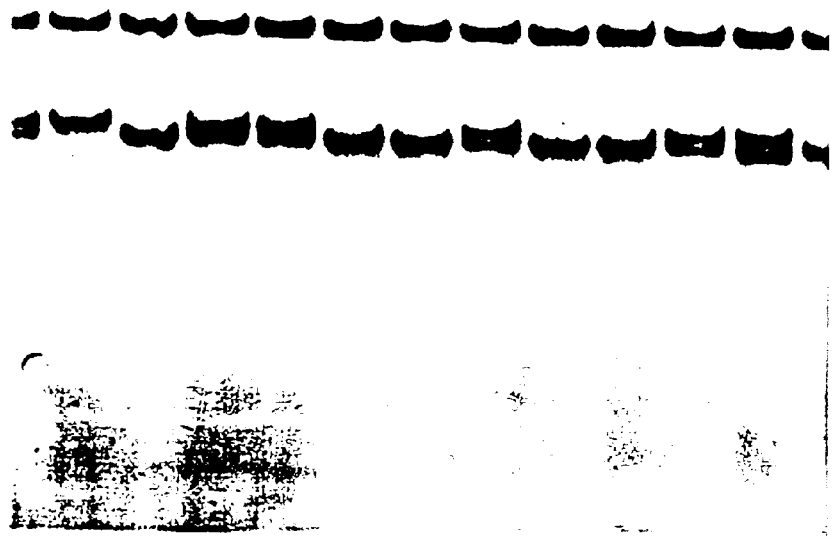
FIG. 1 is a photograph of a single strand conformational polymorphism (SSCP) gel illustrating the polymorphism of the 5' untranslated region of the thyroglobulin gene.

The invention will now be described in detail by way of reference only to the figure and to the following non-limiting examples.

EXAMPLE 1

CSSM66 is Associated with Marbling in Offspring of a Wagyu Sire

In the first experiment, DNA markers were selected from the bovine genetic linkage maps (Barendse et al, 1994, 1997; Bishop et al, 1994) so that a highly polymorphic DNA marker was present on each chromosome. These markers were evaluated for polymorphism on the Wagyu sire and if he was a homozygote an alternative marker was found. The resultant group of DNA markers were evaluated sequentially on the Wagyu offspring for linkage to marbling.

Since the sires and offspring were genotyped but no dams were genotyped, only those offspring that shared one allele with the sire provide direct information on linkage. The offspring that share none consistently were removed from the analysis as they indicate mispaternity. The offspring that share two alleles with the father can provide some information on linkage only if allele frequencies of the marker are known for this population. For these offspring the parental origin of each allele is uncertain, but probabilities of origin can be assigned for different genotypes of the dam, and the occurrence of the genotypes for the dams can be derived from the population frequencies of the alleles. These data are inferential, require a likelihood ratio approach for analysis, and were not used. Clearly, the more alleles to the marker the more information on linkage is available for analysis, since the offspring is more likely to share only one allele with the sire.

The results were analysed by segregating the individuals by marbling score and by paternal allele after parentage testing had been completed. These 2×2 tables were analysed via contingency chi-square analyses to test associations that are not dependent upon a genetic model. They were also analysed by setting expected proportions equal, as if there was a single Mendelian locus on that particular chromosome with an additive effect on marbling.

The fingerprinting of the offspring of the Wagyu sire showed 5 offspring that regularly failed to share a band with the sire, and so they were excluded from further analyses, although the samples were retained since they provided clear landmarks on the autoradiograms. These results are summarized in Table 1.

TABLE 1

Association Between the DNA Marker CSSM66 and the Marbling Score Among Offspring of the Wagyu Sire

| M2 | M4 | Allele |
|---|---|---|
| 49 | 7 | 2 |
| 37 | 26 | 4 |

$\chi^2_1 = 12.24$ p < 0.001

M2 and M4 are marbling scores of 2 and 4 respectively. Allele is the allele of the sire inherited by the steer. Alleles are ranked in mobility, with the fastest migrating allele=1

The polymorphic DNA marker CSSM66 showed an association to marbling score in the offspring of the Wagyu sire, with a probability of less than 0.001 of this occurring by chance. This marker was the 12th in a series of loci chosen at random. The locus RM180 was tested, and found to show a non-significant deviation from the expected values. RM180 is 18 cM distal to CSSM66, indicating that a gene affecting marbling would be in the close vicinity of CSSM66.

EXAMPLE 2

CSSM66 and Marbling in Angus and Shorthorn Offspring

The DNA markers that showed a positive association in the first experiment were tested in the second experiment. They have an a priori expectation of being positively associated, and a lower threshold for significance is acceptable. Two approaches were taken to these data. In the first, the two groups of extreme marbling scores were compared irrespective of ancestry. This rough analysis would show an association if there were linkage disequilibrium between the DNA markers and a locus that affects the marbling score. Irrespective of the prior linkage demonstrated for these regions, however, these results could be biased if they are dominated by a single sire that contributed many individuals of one particular marbling score, where this sire was a homozygote for the DNA marker. In the second approach, only those animals that were drawn at random and were essentially unrelated to others in the study were analysed by marbling groups and by genotype for a population association. For the animals in sire groups, only those from sires that had offspring of low and of high marbling score were retained and the rest excluded. The gene frequencies of the two groups were compared via the chi-square analysis. The relative risk was calculated via the method of Woolf (1955).

CSSM66 was tested over the Angus and Shorthorn offspring irrespective of ancestry, and the results are shown in Table 2.

TABLE 2

Association Between the DNA Marker CSSM66 and Marbling Score Among Angus and Shorthorn Steers

| M1 | M4 | Allele |
|---|---|---|
| 22 | 20 | 1 |
| 11 | 11 | 2 |
| 25 | 28 | 3 |
| 14 | 39 | 4 |
| 5 | 5 | 5 |
| 57 | 52 | 6 |
| 2 | 2 | 7 |

$\chi^2_6 = 5.82$ p < 0.45 n.s.

M1 and M4 are marbling scores of 1 and 4 respectively. Allele is the allele of the steer. Alleles are ranked in mobility with the fastest migrating allele=1, and are comparable to Table 1.

No significant association was found between CSSM66 and marbling score. The allele '4', which had been found linked to high marbling scores in the Wagyu experiment, was twice as common in animals of high marbling but there is no corresponding allele that showed an excess among animals with low marbling.

RM180 showed no association.

EXAMPLE 3

Identification of Thyroglobulin Polymorphism Associated with Marbling

Primers were designed so as to be complementary to the 5' untranslated region (5'UTR) of the thyroglobulin gene (TG: Genbank accession X05380). This sequence contains a homopurine sequence and a copy of the bovine monomeric dispersed repeat (de Martynoff et al, 1987), and the primers were located to include both of these features. The primer sequences are:

```
TG5U2   5'ggg gat gac tac gag tat gac tg 3'  (SEQ ID NO: 1)

TG5D1   5'gtg aaa atc ttg tgg agg ctg ta 3'  (SEQ ID NO: 2)
``` and the expected size of the fragment is 545 base pairs. The fragment was amplified by the polymerase chain reaction (PCR), and tested for polymorphism by single strand conformational analysis (SSCA) using previously described methods (Mullis et al, 1986; Orita et al, 1989; Barendse et al, 1993). The fragments were amplified with an annealing temperature of 55° C. at 2 mM magnesium chloride for at least 30 cycles of the PCR. The fragments were then separated for 22 hours on 0.4 mm gels composed of 8% acrylamide (89:1::acrylamide:bis-acrylamide), 0% glycerol, 0.5×TBE (1×TBE is 0.089 M TrisHCl, 0.089 M boric acid, 0.002 M disodium ethylenediaminetetraacetic acid) in 38 cm wide×50 cm long gels at 3 Watts at room temperature. These conditions provide the best means of separating all three alleles, particularly the rare 1 allele, at this locus, although several different conditions of glycerol (5 and 10 percent) and power (5 and 7 W) provide separation of the alleles 2 and 3. The fragments were detected by autoradiography.

The primers for the 5'UTR of thyroglobulin produce a single fragment, which shows three alleles when run on single strand conformational polymorphism (SSCP) gels, as illustrated in FIG. 1. There are 11 complete genotypes on the gel. The top series of bands is one conformation of the DNA fragment and is uninformative. The bottom series of bands is the alternative conformation which shows three alleles. The genotypes are in the order:

33 22 23 23 22 22 23 22 22 23 13

Five associations were calculated. The first was for all individuals that were sampled at random, as summarized in Table 3. The probability of the association occurring by chance is less than 0.05, with allele 3 being associated with high marbling levels. The relative risk of possessing allele 3 is 3.81.

TABLE 3

Association Between Thyroglobulin and
Marbling Score Among the Angus and
Shorthorn Steers Drawn from the Cattle Population

| Marbling | Genotypes | | |
|---|---|---|---|
| | 22 | 23 | 33 |
| M1/2 | 10 | 7 | 0 |
| M4/5 | 6 | 15 | 1 |

$\chi^2_1 = 3.94$ p < 0.05

M1/2 are low marbling scores and M4/5 are high marbling scores. Genotype is the genotype of the steer. Allele 1 is extremely rare, and only 2 copies of this allele have been seen in 264 individuals.

The one genotype of '33' was merged with the '23' genotypes for the M4/5 class to calculate the chi-square. The relative risk for the '3' allele and increased marbling is 3.81.

In the second association, the steers compared were derived from sires who produced steers of high and of low marbling, and again there is a small sample size. The results are summarized in Table 4. This association shows the same direction, where allele three is associated with high marbling scores, and has a probability less than 0.05 of occurring by chance.

TABLE 4

The Association Between Thyroglobulin and Marbling
Score Among the Angus and Shorthorn Steers Drawn from
Families Where the Sire and Offspring of High
and of Low Marbling Score

| M1/2 | M4/5 | Allele |
|---|---|---|
| 60 | 45 | 2 |
| 22 | 33 | 3 |

$\chi^2_1 = 4.25$ p < 0.04

M1/2 are low marbling scores and M4/5 are high marbling scores. Allele '1' is extremely rare and only 2 copies of this allele have been seen in 264 individuals.

EXAMPLE 4

DNA Sequence of the Thyroglobulin Alleles
TG5U2 and TG5D1 Described in Example 3

The DNA sequence of the thyroglobulin gene, amplified by the primers TG5U2 and TG5D1 described in Example 3, shows three alleles in the study population. These alleles were isolated, and the DNA sequence of each was determined using the standard dideoxy sequencing method (Sanger et al, 1977). The numbering of the alleles corresponds to that in FIG. 1. The DNA sequence of each allele is given in Table 5, and the DNA sequence differences responsible for the variation are highlighted.

TABLE 5

The Sequences of Three of the Alleles Amplified by the TG5U2 and TG5D1 Primers.

The sequence differences that define the alleles are in bold capital letters

Allele 1 (SEQ ID NO: 3)

ggggatgactacgagtatgactgtgcgtgtgtttggcttatctcatcaaaatctctaca ttctgtgttaatggatctgcctgttttgttccctgccatatcctcatggcctagaatag tgtctgcttctctatcagactctaaagaaacattgctaggagggaaggaaggagcatgg atgaggagggagggagcattgtgtttctctcacggtgggcctgaacgtgtggcccacca agttgttaactttggcctttacccctgaagatgaattatgaagccacacccccagttct tccttggtggctcagatggtcaagaatccacctgcaatgcgggagacctgggtttgatc cctggggttgggaagatCccctggagaagggaatggctacccactccagtattctggcct ggagaatcccatggacagaggagcctggcgggatgcagtccatgggtctcagagagtc agatgtgactgagcgactttcacacacaCtcgtccctggttctgctcccctacagcctc cacaagattttcac Allele 2 (SEQ ID NO: 4)

ggggatgactacgagtatgactgtgcgtgtgtttggcttatctcatcaaaatctctaca ttctgtgttaatggatctgcctgttttgttccctgccatatcctcatggcctagaatag tgtctgcttctctatcagactctaaagaaacattgctaggagggaaggaaggagcatgg atgaggagggagggagcattgtgtttctctcacggtgggcctgaacgtgtggcccacca agttgttaactttggcctttacccctgaagatgaattatgaagccacacccccagttct tccttggtggctcagatggtcaagaatccacctgcaatgcgggagacctgggtttgatc cctggggttgggaagatcccctggagaagggaatggctacccactccagtattctggcct ggagaatcccatggacagaggagcctggcgggatgcagtccatgggtctcagagagtc agatgtgactgagcgactttcacacacaTtcgtccctggttctgctcccctacagcctc cacaagattttcac Allele 3 (SEQ ID NO: 5)

ggggatgactacgagtatgactgtgcgtgtgtttggcttatctcatcaaaatctctaca ttctgtgttaatggatctgcctgttttgttccctgccatatcctcatggcctagaatag tgtctgcttctctatcagactctaaagaaacattgctaggagggaaggaaggagcatgg atgaggagggagggagcattgtgtttctctcacggtgggcctgaacgtgtggcccacca agttgttaactttggcctttacccctgaagatgaattatgaagccacacccccagttct tccttggtggctcagatggtcaagaatccacctgcaatgcgggagacctgggtttgatc cctggggttgggaagatTccctggagaagggaatggctacccactccagtattctggcct ggagaatcccatggacagaggagcctggcgggatgcagtccatgggtctcagagagtc agatgtgactgagcgactttcacacacaTtcgtccctggttctgctcccctacagcctc cacaagattttcac

EXAMPLE 5

Thyroglobulin Polymorphism in Wagyu Offspring

For the thyroglobulin polymorphism, the offspring of the Wagyu sire were analysed retrospectively to determine whether there was an association to marbling score and whether this association was in the same general direction as that found in the Angus and Shorthorn steers. Since the Wagyu samples were collected from three different feedlots at three different times, these samples were analysed separately. Furthermore, since there are only effectively two alleles at the thyroglobulin polymorphism (see below), this locus was analysed for population association rather than genetic linkage, using goodness of fit contingency chi-squares, since the allelic contribution of the sire cannot be ascertained in the heterozygotes as the maternal genotypes are not available. In two of the three Wagyu subsamples there were insufficient individuals with extreme marbling scores, so all the marbling scores were analysed.

The probabilities (P) of the independent chi-squares were transformed using natural logarithms and summed (Sokal and Rohlf, 1981) to form a combined probability estimate for the association between thyroglobulin and marbling. The value of $-2\Sigma \ln P$ is distributed as a chi-square with the number of degrees of freedom equal to twice the number of component probabilities.

The third, fourth and fifth associations were tested among the Wagyu offspring. Two of these three associations have probability values less than 0.05 of occurring by chance when the genetic model is assumed to be dominant inheritance; having one copy of the '3' allele gives the same effect as having two copies of the '3' allele. None of the associations has a probability level below 0.05 when a codominant model is assumed. Of these three associations, one uses the extremes of marbling, as shown in Table 6.

TABLE 6

The First Sample of Wagyu Steers that are Extreme for Marbling Genotyped for the Thyroglobulin Polymorphism.

| Genotype | Marbling | |
|---|---|---|
| | M2 | M4 |
| 22 | 44 | 5 |
| 23 | 33 | 12 |
| 33 | 6 | 2 |

$\chi^2_1 = 4.41 \; p < 0.04$ (A: Dominant mode)
$\chi^2_2 = 4.43 \; p < 0.11$ (B: Co-dominant mode)

Two genetic models are used. Model 1 assumes a dominant mode of inheritance, and model 2 assumes a co-dominant mode of inheritance.

Note: The 33 genotypes were added to the 23 genotypes to get the dominant mode.

The thyroglobulin genotypes were compared to the marbling scores, and an association between higher marbling score and the possession of one or more copies of the '3' allele was formed, with a probability less than 0.05 of occurring by chance. For the two other associations the thyroglobulin genotypes were compared to all the marbling scores, since these subsamples had insufficient numbers of animals with extreme marbling scores for statistical significance to be demonstrated. These results are summarized in Tables 7 and 8.

TABLE 7

The Second Sample of the Wagyu Steers: Analysis of the Trend to Higher Marbling Score Among Individuals of the 23 Genotype

| Genotype | Marbling Score | | | | |
|---|---|---|---|---|---|
| | M2 | M3 | M4 | M5 | M6 |
| 22 | 10 | 16 | 6 | 3 | 0 |
| 23 | 14 | 23 | 23 | 7 | 2 |
| 33 | 3 | 4 | 5 | 2 | 0 |

$\chi^2_1 = 4.20 \; p < 0.05$ (A: 22 vs 23/33)
$\chi^2_2 = 4.68 \; p < 0.10$ (B: Co-dominant)

There were insufficient animals of extreme marbling score to analyse only the extremes.

Instead of extremes being compared, M2 plus M3 is compared to M4, M5 plus M6.

TABLE 8

The Third Sample of the Wagyu Steers: Analysis of the Trend to Higher Marbling Score Among Individuals of the 23 Genotype

| Genotype | Marbling Score | | | | |
|---|---|---|---|---|---|
| | M2 | M3 | M4 | M5 | M6 |
| 22 | 4 | 28 | 5 | 1 | 0 |
| 23 | 11 | 48 | 7 | 1 | 0 |
| 33 | 0 | 5 | 1 | 1 | 0 |

$\chi^2_1 = 0.11 \; p < 0.75$ (A: 22 vs 23/33)
$\chi^2_2 = 1.54 \; p < 0.47$ (B: Co-dominant)

There were insufficient animals of extreme marbling score to analyse only the extremes.

Instead of extremes being compared, M2 plus M3 is compared to M4, M5 plus M6.

The numbers of individuals with marbling scores M2 and M3 were combined and compared to the combined number for marbling scores of M4, M5 and M6. One of the two samples showed an association between possession of one or more copies of the '3' allele and higher marbling scores (Table 7), with a probability less than 0.05 of occurring by chance. The other sample (Table 8) showed no association of thyroglobulin with marbling score. In no case was there an association between possession of the '22' genotype and high marbling score.

The probabilities for the five thyroglobulin tests were summed in two ways as three of the five tests having two models—dominant and co-dominant. The results are shown in Table 9.

TABLE 9

The Combination of Chi-Square Probabilities for all the Associations Between Thyroglobulin and Marbling

| | Chi-Square | | P | 1 nP |
|---|---|---|---|---|
| 1. | $\chi^2_1 = 3.94$ | | p = 0.047 | −3.058 |
| 2. | $\chi^2_1 = 4.25$ | | p = 0.039 | −3.244 |
| 3. | $\chi^2_1 = 4.41$ | A | p = 0.036 | −3.324 |
| | $\chi^2_2 = 4.43$ | B | p = 0.109 | −2.216 |
| 4. | $\chi^2_1 = 4.20$ | A | p = 0.040 | −3.219 |
| | $\chi^2_2 = 4.68$ | B | p = 0.096 | −2.216 |
| 5. | $\chi^2_1 = 0.11$ | A | p = 0.745 | −0.294 |

TABLE 9-continued

The Combination of Chi-Square Probabilities for all
the Associations Between Thyroglobulin and Marbling

| Chi-Square | | P | 1 nP |
|---|---|---|---|
| $\chi^2_2 = 1.54$ | B | p = 0.464 | −0.768 |
| $\chi^2_5 = 26.278$ | | p < 0.005 (A) | |
| $\chi^2_5 = 23.258$ | | p < 0.005 (B) | |

All associations bar one show an association between the 3 allele and high marbling score, one test showing no association. The A series represents the dominant mode of inheritance, while the B series represents the co-dominant mode.

The two combinations are thus all the dominant models and all the co-dominant models. Both of these summations have probabilities less than 0.005 of occurring by chance, and are extremely significant.

The Wagyu sire is a heterozygote for this polymorphism, with the genotype '23'. Among the 335 offspring of the Wagyu sire tested none showed the '1' allele.

EXAMPLE 6

Chromosome 5 is Associated with Marbling in Offspring of a Wagyu Sire

Surprisingly also, significant associations to marbling score were found with the anonymous DNA markers CSSM34 and ETH10 and these will be described in the next several examples. These markers had been assigned to bovine chromosome 5 on the International Bovine Reference Family Panel (described in Barendse et al, 1997), with a location about one third of the way down the chromosome. Using the Wagyu family material described in Example 1 above, DNA markers from chromosome 5 were genotyped on the Wagyu sire and his offspring. The DNA marker from chromosome 5 with the best association in the 2×2 contingency chi-square is ETH10 (Toldo et al, 1993), as shown in Table 10.

TABLE 10

Association Between the DNA Marker ETH10 and the
Marbling Score Among Offspring of the Wagyu Sire

| M2 | M4 | Allele |
|---|---|---|
| 60 | 12 | 2 |
| 24 | 17 | 5 |

$\chi^2_1 = 8.42$   P < 0.005
$\chi^2_1 = 16.28$  P < 0.0001   (Dominant model)

M2 and M4 are marbling scores of 2 and 4 respectively. Allele is the allele of the sire and that the steer inherited. Alleles are ranked in mobility, with the fastest migrating allele=1. Allele 2 is 217 bp long and allele 5 is 223 bp long. Other lengths of alleles are expected at the ETH10 DNA marker.

The polymorphic DNA marker ETH10 showed an association to marbling score in the offspring of the Wagyu sire, with a probability of less than 0.005 of this occurring by chance, and with a probability of less than 0.0001 of this occurring by chance if a dominant mode of inheritance is assumed. This marker was the tenth in a series of loci chosen at random. This association indicated that a gene affecting marbling would be in the close vicinity of ETH10. Allele 5 of ETH10 was associated with higher marbling scores, while allele 2 was associated with lower marbling scores. The marker CSSM34 showed no association with marbling in this family: the sire provided informative meioses, but there was no evidence for segregation of marbling near CSSM34.

EXAMPLE 7

Chromosome 5 Markers and Marbling in Angus and Shorthorn Steers

Figure 2:
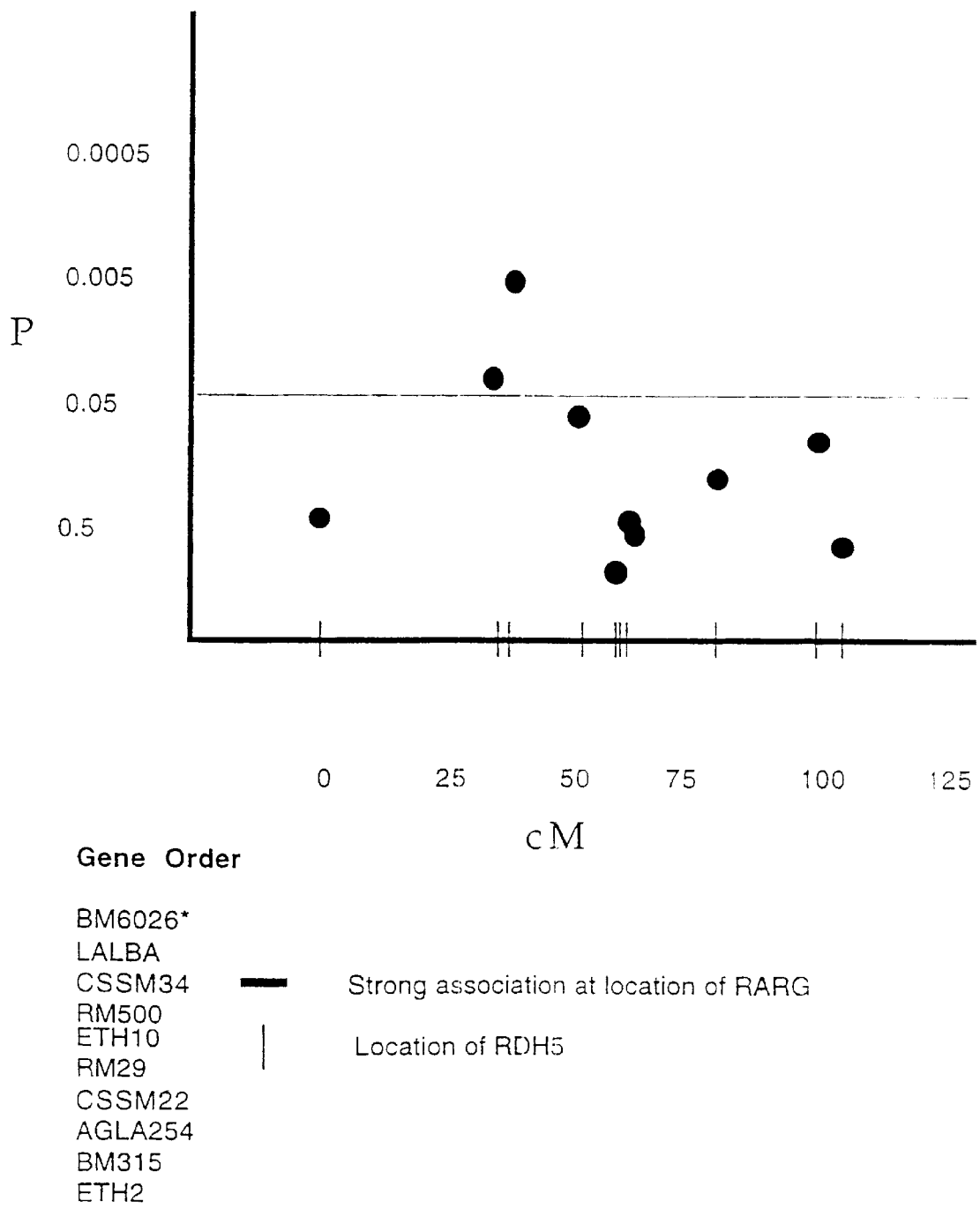
FIG. 2 shows the results of tests of associations between DNA markers or chromosome 5 and the marbling score.

A series of DNA markers from chromosome 5 which are located on either side of ETH10 were tested on a sample of Angus and Shorthorn steers of known ancestry. These are the same steers as those used in Example 2. The analysis was performed so that at most two steers from each grandsire were used. Only steers of extreme marbling score were used, so that a comparison of extreme marbling scores was made across a cross-section of the beef industry. The DNA marker CSSM34 (Moore et al, 1994) had the most significant association with marbling, as shown in Table 11, and the pattern of association of marbling to the DNA markers shows that a marbling gene on chromosome 5 is located in close proximity to CSSM34, as shown in FIG. 2. ETH10 showed no association to marbling in these Angus and Shorthorn steers.

TABLE 11

Association Between the DNA Marker CSSM34
and the Marbling Score Among Offspring
of Known Angus and Shorthorn Sires

| | ALLELE | | | | | |
|---|---|---|---|---|---|---|
| MARBLING | 1 | 2 | 3 | 4 | 5 | 6 |
| M1 | 3 | 31 | 14 | 5 | 18 | 9 |
| M4+ | 1 | 49 | 24 | 5 | 7 | 2 |

$\chi^2_5 = 16.63$   P < 0.0053

M1 and M4+ are marbling scores of 1 and greater than or equal to 4 respectively. Allele is the allele that the steer possesses. Alleles are ranked in mobility, with the fastest migrating allele=1. The alleles differ in size, hence the differences in mobility, and allele 1=100 bp (base pairs), allele 2=102 bp, allele 3=106 bp, allele 4=108 bp, allele 5=110 bp and allele 6=112 bp. Other alleles with different sizes are expected to exist.

The association between marbling and CSSM34 is strong, and has a probability of less than 0.0053 of occurring by chance. Since a marbling gene had already been demonstrated through the association with ETH10 in Example 6, this association provides strong evidence of the existence of a gene affecting marbling score on chromosome 5. No other DNA marker tested for chromosome 5 had as strong an association with marbling. The next best association was to the gene LALBA, but that had a probability only slightly less than 0.05 of occurring by chance. Since LALBA has a genetic distance of approximately 2 cM from CSSM34 (Barendse et al, 1997), this indicates that CSSM34 is in close allelic association with a marbling gene.

Several of the alleles of CSSM34 show allelic association with marbling. Notably alleles 2 and 3 are associated more with higher marbling scores, while 5 and 6 are associated with lower marbling scores.

EXAMPLE 8

CSSM34 Evaluated on Randomly Drawn Angus and Shorthorn Steers of Unknown Ancestry CSSM34 was then tested on randomly-collected Angus and Shorthorn steers of unknown ancestry. Firstly, a positive association would confirm the results found in steers of known ancestry. If the results showed the same pattern of allelic disequilibrium this would indicate that the marker CSSM34 was not only a robust predictor of marbling capacity, but that it was extremely closely associated with the causal mutation for marbling. Secondly, a positive association would indicate that the marker CSSM34 could be used as a tool in feedlots to draft animals into particular feeding regimes on the basis of their genotype, and in that way alter the probability of achieving desired marbling scores.

The sample of cattle for this experiment was obtained by bleeding 50 to 100 cattle each week of the Angus or Shorthorn breed of unknown parentage from the same abbatoir. In addition to the breed identification, the identity of the vendor was recorded as well as the standard chiller room and feedlot data such as marbling score, subcutaneous fat thickness, age, feeding regime and carcass weight. By sampling each week and by maximizing the number of vendors that were present in a sample, a wide cross section of the beef industry was obtained. There are an average of five steers per vendor in the sample with a total of 162 vendors. DNA was extracted from all available blood samples. The data form a contingency table with marbling scores as the rows and the allele possessed by the individual as the columns. The contingency data were analysed using the G statistic (Sokal and Rohlf, 1981), since some of the cells had small expected numbers and the G statistic provides a superior approximation to the chi-square distribution.

The association between CSSM34 and marbling in the randomly-collected Angus and Shorthorn steers is shown in Table 12.

TABLE 12

Association Between CSSM34 and Marbling Scores for Randomly Collected Angus and Shorthorn Steers of Unknown Ancestry

| MARBLING | ALLELE | | | | | |
|---|---|---|---|---|---|---|
|  | 1 | 2 | 3 | 4 | 5 | 6 |
| M1 | 4 | 35 | 35 | 11 | 8 | 9 |
| M2 | 8 | 257 | 261 | 47 | 89 | 66 |
| M3 | 4 | 213 | 158 | 24 | 41 | 33 |
| M4 | 2 | 80 | 58 | 11 | 16 | 7 |
| M5 | 0 | 13 | 8 | 1 | 2 | 0 |

$G_{adj} = 32.17$   df 20   $P < 0.05$

M1 to M5 are marbling scores of 1 through to 5. Allele is the allele that the steer possesses. Alleles are ranked in mobility, with the fastest migrating allele=1, and are the same designations as in Table 11. $G_{adj}$ is the G statistic adjusted using the Williams correction (Sokal and Rohlf, 1981).

This comparison shows that there is clearly an allelic association between marbling score and allele at the DNA marker CSSM34, and is consistent with the previous analyses. Since the animals are sampled at random from the population and their ancestry is unknown, our result confirms that this marker can predict average marbling score without knowing the ancestry of a steer. When allele 2 is compared to allele 6 from Table 12 the $G_{adj}=15.21$, df 4, P<0.005, indicating that there is a highly significant difference in marbling score for those with allele 2 compared to those with allele 6. This association between alleles 2 and 6 and marbling is consistent with the previous sample, shown in Table 11, which indicates that the allelic association is not only consistent but is also stable. Such associations occur when the polymorphism is responsible, or where the marker is closely associated with the responsible gene.

EXAMPLE 9

CSSM34 is Closely Associated with the Retinoic Acid Receptor Gamma (RARG) Gene While ETH10 is Closely Associated with the Retinol Dehydrogenase 5 (RDH5) Gene No immediate candidate genes for marbling were evident, although several adipocyte differentiating factors were expected to be on chromosome 5 on the basis of their genomic locations in humans and mice. CSSM34 is located very close to collagen 2 alpha 1 (COL2A1), but that gene is not a candidate gene for marbling. Based on the human map near COL2A1, two candidate genes suggested themselves. These are the genes for retinoic acid receptor gamma (RARG) and 11-cis and 9-cis retinol dehydrogenase (RDH5). RARG is a nuclear receptor for all-trans retinoic acid, which is derived from retinol, and RDH5 catalyses the interconversion of 11-cis and 9-cis retinol to 11-cis and 9-cis retinoic acid (Mertz et al, 1997). The level of retinol (vitamin A) in the blood is linearly related to marbling score (Torii et al, 1996), and the retinoic acid receptors are known factors in the differentiation of pre-adipocytes (Ailhaud et al, 1992; Darimont et al, 1993; Smas and Sul, 1995). Importantly, the concentration of retinol has an impact on marbling score but no impact on the thickness of subcutaneous fat, suggesting that DNA tests for this region could identify a propensity for increase marbling without necessarily also increased fat levels in other fat depots of cattle. A standard treatment in Japan to enhance marbling score is to reduce the level of vitamin A precursors such as β-carotene in the diet of the steer. RDH5 has been sequenced in cattle, but RARG had not previously been sequenced and a DNA clone had not been isolated.

We sought to identify the genes with which the DNA markers CSSM34 and ETH10 were associated. The first stage was to identify fragments from the bovine RARG and RDH5 genes and locate these on the bovine chromosomes at high resolution relative to the CSSM34 and ETH10 polymorphisms. A whole-genome radiation hybrid panel (Womack et al, 1997) was used to locate CSSM34 and ETH10 relative to several genes and DNA markers from chromosome 5. RDH5 proved to be close to ETH10, at a distance of 1.01 centi-Rads (cR). RARG proved to be close to CSSM34, at a distance of 3.25 cR. These distances represent extremely close physical distances, and these DNA markers are clearly closely associated with the respective genes. The primers for CSSM34 and for RARG were then used to probe a Yeast Artificial Chromosome (YAC) library, and every DNA clone that was positive for CSSM34 was also positive for RARG. We have thus identified cloned DNA fragments for the cattle RARG gene, and all of these contain the CSSM34 DNA marker. A RARG-associated polymorphism, CSSM34, can be used to predict marbling score in, but not limited to, the Angus and Shorthorn breeds of cattle. Further, a RDH5 associated polymorphism, ETH10, is linked to marbling in the Wagyu breed of cattle.

The bovine sequence for RDH5 (Genbank accession X82262, Simon et al, 1995) was used to design primers for RDH5. The primers RDH5U and RDH5D generate a 282 bp fragment from bovine DNA. This fragment is polymorphic in cattle, with two alleles.

No bovine sequence for RARG has been described, so the human and mouse sequences were used to generate fragments from bovine DNA. The human sequence for RARG (Genbank accession M38258, Lehmann et al, 1991) and the mouse sequence for RARG (Genbank accession M34476, Giguere et al, 1990) were obtained to design heterologous primers for RARG. Primers were used to amplify the intron between exon 6 and exon 7, and the amplified fragment was cloned and sequenced using standard dideoxy sequencing methods (Sanger et al, 1977). The fragment was analysed using fluorescent labelling via the ABI cycle sequencing protocol (Perkin Elmer, Foster City, Calif., USA) to confirm that RARG was cloned in cattle. The sequence is shown in Table 13. Primers (RARGSJ1U, RARGSJ1D) derived from this sequence amplify bovine DNA. Other primers were also designed to amplify RARG from bovine DNA (RARGE3U1, RARGE3D1 and RARGE8U2, RARGE8D1). The sequences of these primers are shown in Table 14, together with the sequences for primers RDH5U and RDH5D for RDH5, and primers ETH10U and ETH10D for ETH10.

TABLE 13

| The DNA Sequence for the Cloned Fragment of Cattle RARG |
| --- |
| (SEQ ID NO: 8) |
| tatgatacnaattcgagctcggtacctacatgttcccaaggatgctaatgaagatcact |
| gacctccggggcatcagcaccaagggttagtcgggagcaagcctcccctctgtcttctc |
| ggagctgccggtctcccaggtcaggcagagacaagagcanagtggggtataatcaggca |
| gcctgcactcgcatcctcgctccgctgcatgctagtgggaacacttggtgcaaaatacc |
| tttccttttgtaccttgtttttctgtttgtgaggatgaaacaagttaacacacaacag |
| gcctacagctgtgctgagttataaagttcagtgcctcctgccctggatggagcagatgt |
| ttccancatcacaggaangttgattggacgcctggcacgcggtgtttgatgaatgtta |
| gtcntagtgataaatgttattaagaacagccatgggcttacggaggggtccanngtgtg |
| tggctggaagtgggcgctgtgtgatcttggaggagacagcctgaaagaaagtgggcagt |
| ggacttggcagagaagacaggcagagttccaggcagaggagtgggccccaggagcttta |
| cagtagaaagagggagagaaagaagcagacagagataacaggcctgtgatgggagcccc |
| agagggcagtcaagcagagttagggaggccgccgtaggtgctgtacntcagcccctga |
| actcttgttcntccactgcaggagcagaaagggccattaccctgaagatggagattcca |
| ggcccgatgcctccctgatccgagaaatgctggagaaccccgaaatgtttgaggacga |
| ctcctcgcagcctggccctcaccccaaggcctctagcgaggatgaggttcctggggatc |
| ctctagagtcgacctgcaggcatgcaagctaggcactggccgtcgttttacaacaa |

TABLE 14

| Oligonucleotide Primers for Amplification of DNA Encoding RARG | | |
| --- | --- | --- |
| RARGSJ1U | 5' cca agg atg cta atg aag atc ac 3' | (SEQ ID NO: 9) |
| RARGSJ1D | 5' gac taa cat tca tca aac acc gc 3' | (SEQ ID NO: 10) |
| RARGE3U1 | 5' ccg cga caa aaa ctg tat ca 3' | (SEQ ID NO: 11) |
| RARGE3D1 | 5' ttg ctg acc ttg gtg atg ag 3' | (SEQ ID NO: 12) |

TABLE 14-continued

Oligonucleotide Primers for Amplification of
DNA Encoding RARG

| | | |
|---|---|---|
| RARGE8U2 | 5' aat ccg aga gat gct gga ga 3' | (SEQ ID NO: 13) |
| RARGE8D1 | 5' cac ccc tag aaa ctt tgg ca 3' | (SEQ ID NO: 14) |
| RDH5U | 5' atg cca agc tgc tct ggt t 3' | (SEQ ID NO: 15) |
| RDH5D | 5' tga agt gac tgt ttt atg cca cac 3' | (SEQ ID NO: 16) |
| ETH10U | 5' gtt cag gac tgg ccc tgc taa ca 3' | (SEQ ID NO: 17) |
| ETH10D | 5' cc tcc agc cca ctt tct ctt ctc 3' | (SEQ ID NO: 18) |

The loci CSSM34, RARG (primers RARGSJ1U and RARGSJ1D) and RDH5 as well as LALBA, ETH10 and CSSM22 (Moore et al, 1994) were genotyped on the whole genome radiation panel of Womack and associates (1997). The results of these genotypes are shown in Table 15.

TABLE 15

The Genotypes for the 6 loci LALBA, CSSM34, RARGSJ1, ETH10, CSSN22 and RDH5
from the Whole Genome Radiation Hybrid Panel of Cattle

| Locus | Radiation Panel Clones |
|---|---|
| LALBA | 000000000000000000011010010000001000100000011100000000001000100000100000110001010000001 |
| CSSM34 | 000000000000000000010010011000001000100000011100000000001000100000100000110001110000001 |
| RARGSJ1 | 000000000000000000010010011000001000101000011100010000001000100000100000110001110100001 |
| ETH10 | 000000000100000000001000010000100000000000100101010000010000000000100010110001010000011 |
| RDH5 | 000000010100000000001000010000100000000000100101010000010000000000100010110001010000011 |
| CSSM22 | 000000010100000000001000010100100000000000010001000000000000000010001011100010100000011 |

The 0 and 1 symbols represent presence or absence of the locus in a particular radiation hybrid clone. The closer two loci are, the more hybrid clones they have in common, and the fewer the differences between them.

The hybrid clone data place RARGSJ1 between LALBA and CSSM34, with a 3.25 cR distance between RARGSJ1 and CSSM34. This is equivalent to a few hundred kilobase pairs between the amplified DNA fragments. These data also place RDH5 1.01 cR from ETH10. Alternatively, CSSM34 is 54 cR from RDH5, a substantial physical distance.

The small relative distance between CSSM34 and RARGSJ1 indicates that both DNA fragments may be contained on a single DNA clone. To test this proposition, a YAC (Yeast Artificial Chromosome) library was screened by hybridization with both of the primers for CSSM34 after these primers were end-labelled with $^{32}P$ γ ATP using Polynucleotide Kinase (Richardson, 1981). The yeast library is contained in the yeast strain AB1380 with the bovine DNA contained in the vector pYAC4. This library was constructed using the methods of Libert and coworkers (1993), and has been deposited in the Resource Centre of the German Human Genome Project http://web.rzpd.de/index.html). Positive clones were identified by autoradiography. The library was also screened with both primers for RARGE8 after the primers were end-labelled with $^{32}P$ γ ATP. Positive clones were identified by autoradiography, and all positive clones were the same as the positives for CSSM34. The clone names are 77D3, 77E3, 71G8, 94B4 and 71E4. This demonstrates that CSSM34 is closely associated with the genomic sequence of RARG.

DISCUSSION

The linkage between CSSM66 and marbling strongly suggests that a locus affecting marbling is located on bovine chromosome 14. The lack of association to RM180 indicates that candidate genes for the effect will be located close to CSSM66, which is located to the proximal third of the chromosome (Barendse et al, 1997). The lack of a gross association between alleles of CSSM66 and marbling indicates that the causative gene is not very close to CSSM66. The gene for thyroglobulin is located some 7 cM from CSSM66, and this gene shows an extremely significant association with marbling score, consistent with a marbling gene on chromosome 14.

Thyroglobulin is encoded by a massive 300 kilobase stretch of genomic DNA. This protein acts as the molecular store for triiodothyronine and tetraiodothyronine (Parma et al, 1987), hormones that are known to have an effect on adipocyte differentiation. It has been known for a half a century (Salter, 1950) that the thyroid hormones are associated with the deposition of fat cells in muscle. Recent experiments in cell culture have shown the role of these hormones in the growth and differentiation of adipocytes (Levacher et al, 1984; Darimont et al, 1993). Furthermore, structural mutational variation in the thyroglobulin gene has been shown to be causally implicated in congenital goitre in Afrikander cattle (Ricketts et al, 1985), so it is unlikely that structural mutations at this gene would be responsible for variation in fat cell differentiation. In addition, the thyroglobulin genomic DNA sequence is unusually low in variation both in humans and cattle (Baas et al, 1984; Georges et al, 1987), suggesting tight control through natural selection.

Alterations in the processing of iodine are likely to have catastrophic results, as can be seen when the diet of humans is deficient in iodine, an element critical to the production of thyroid hormones. The consequences of this deficiency are cretinism, failure of proper development and growth of the bones resulting in a high body weight to length ratio, and myxoedema. The level of the thyroid hormones is implicated in adipocyte differentiation and has an effect on metabolic rate, which in turn has an impact upon the amount of energy available for storage.

Since the 5' untranslated regions (5'UTR) of genes are critical in transcription and translation (Ptashne, 1988, Kozak, 1991), and hence affect the level and availability of a protein, a DNA polymorphism was sought in the 5'UTR of thyroglobulin. The novel polymorphism identified in this specification shows an association to marbling which has a consistent direction, in which allele '3' is associated with higher marbling scores in four of five subdivisions of the data. For a small sample of unrelated animals the relative risk of allele '3' compared to allele '2' was 3.81; thus animals with high marbling score are almost 4 times more likely to have at least one copy of allele '3' than to be a '22' homozygote. Consistent with this model, the Wagyu sire is a '23' heterozygote and segregates marbling score on chr. 14. It would have been a powerful test of this fragment had he been a homozygote. The overall probability level for the association between marbling score and this thyroglobulin polymorphism is very strong, being less than 0.005, and the evidence for marbling gene on chromosome 14 is convincing, being probability level for the association less than 0.0001 irrespective of the mode of inheritance.

Due to linkage disequilibrium, polymorphisms located near to thyroglobulin on chromosome 14 will also have some predictive value for marbling. However, CSSM66 is not one of them, consistent with the 7 cM distance between CSSM66 and thyroglobulin; linkage disequilibrium is usually expected when the genetic distance is low, generally when it is less than 3 cM. Nevertheless, unless it is proved that there are other likely genes affecting marbling in this region of chromosome 14 it must be assumed that these other polymorphisms are predicting the same test described in this report. Polymorphisms in the 5'UTR of the thyroglobulin molecule of other mammalian species may predict levels of fat in those species, since the action of the iodothyronines is conserved across species, and the structure of thyroglobulin is relatively strongly conserved. There is 84% homology of sequence between humans and cattle, and 75% homology between mice and cattle.

Obviously, marbling is affected by the products of several genes as well as being subjected to environmental influences, so one genetic test will not cover all the variation. Thus, some '33' homozygotes are expected to have low marbling scores due to the influence of variation at other genes or of suboptimal management. Nevertheless, selection of animals on the basis of the thyroglobulin polymorphism described here will shift the proportions of animals that show high and low levels of marbling, either in feedlots or when selecting parents to generate steers.

CSSM66 has been shown to be linked to milk fat percentage in USA Holstein dairy cattle (Ron et al, 1996), so it is expected that the polymorphism in the thyroglobulin gene described here will be predictive in the selection of cattle for high levels of milk fat, since the thyroid hormones are known to have an impact on the fat percentage of milk (Folley and Malpress, 1948).

The linkage between both ETH10 and CSSM34 and marbling indicates that one or more loci affecting marbling occurs on bovine chromosome 5. The replicated, strong population association with CSSM34, and the weak association to the nearby gene LALBA indicate that a locus affecting marbling is closely associated with CSSM34. The gene for RARG is closely associated with CSSM34, and occurs in the same DNA clone with it. On the basis of biochemical evidence, RARG is a strong candidate gene for the effect, as it is a ligand for all-trans retinoic acid (Mertz et al, 1997), and the concentration of retinol in the serum is directly related to the marbling score of a steer (Torii et al, 1996), but unrelated to subcutaneous fat thickness. This indicates that RARG is the likely locus affecting marbling. Nevertheless, CSSM34 is not the only predictor of marbling score in this genomic region, and markers on either side of CSSM34 will also act to predict marbling, just as LALBA is a weak predictor of marbling capacity due to its close proximity. The gene encoding the Roan factor (Charlier et al, 1996) is in the same genomic region as CSSM34, and so, in breeds that segregate the Roan factor, the colour of a steer will be associated with marbling score in some families. These polymorphisms must be assumed to be predicting a locus affecting marbling in and around the RARG gene in cattle.

The fact that the Wagyu data (Example 6) show a peak at ETH10, some 20 cM or 54 cR from CSSM34 (Barendse et al, 1997), may indicate that there is more than one gene for marbling on chromosome 5. The ETH10 polymorphism shows no association to marbling in the Angus and Shorthorn, while the CSSM34 polymorphism shows no association to marbling in the Wagyu offspring. The gene RDH5, catalysing the conversion of 11-cis and 9-cis retinol to 11-cis and 9-cis retinoic acid, is extremely closely associated with ETH10. Indeed, the association of ETH10 with RDH5 is closer than that of CSSM34 with RARG. Again, the level of retinol in the serum is directly related to marbling score in cattle, and an enzyme catalyzing the conversion of retinol to retinoic acid would affect the availability of retinoic acid for binding to the retinoic acid receptors. RDH5 is thus a strong candidate for a locus affecting marbling in Wagyu-derived cattle. Other polymorphisms near ETH10 and RDH5 would also show linkage to marbling, and those polymorphisms must be assumed to be predicting the same locus affecting marbling score in and around the RDH5 gene in cattle. The total evidence for a marbling gene on chromosome 5 is convincing, with a combined probability of less than 0.00015 of being due to chance.

RDH5 and RARG should act in concert, and since they are approximately 20 cM apart, it is likely that some animals will have chromosomes that have a favourable allele for marbling at one locus and an unfavourable allele for marbling at the other locus, cancelling each other out. Progress to improve marbling would be slow if those animals were used in breeding schemes using conventional methods. However, with the DNA marker tests specified here, it will be a simple matter to breed cattle that have alleles favourable for marbling at both genes. Naturally, the breeding would also use the TG marker on chromosome 14, which is expected to be associated with fatness in general in addition to marbling, to generate steers of consistent and optimal marbling score.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

Ailhaud, G., Grimaldi, P. and Negrel, R. Annual Review of Nutrition, 1992 12 207–233

Barendse, W., Armitage, S. M., Kossarek, L. M., Shalom, A., Kirkpatrick, B. W., Ryan, A. M., Clayton, D., Li, L., Neibergs, H. L., Zhang, N., Grosse, W. M., Weiss, J., Creighton, P., McCarthy, F., Ron, M., Teale, A. J., Fries, R., McGraw, R. A., Moore, S. S., Georges, M., Soller, M., Womack, J. E. and Hetzel, D. J. S. Nature Genetics, 1994 6 227–235

Barendse, W., Armitage, S. M., Ryan, A. M., Moore, S. S., Clayton, D., Georges, M., Womack, J. E. and Hetzel, J. Genomics, 1993 18 602–608

Barendse, W., Vaiman, D., Kemp, S. J., Sugimoto, Y., Armitage, S. M., Williams, J. L., Sun, H. S., Eggen, A., Agaba, M., Aleyasin, S. A., Band, M., Bishop, M. D., Buitkamp, J., Byrne, K., Collins, F., Cooper, L., Coppettiers, W., Denys, B., Drinkwater, R. D., Easterday, K., Elduque, C., Ennis, S., Erhardt, G., Ferretti, L., Flavin, N., Gao, Q., Georges, M., Gurung, R., Harlizius, B., Hawkins, G., Hetzel, J., Hirano, T., Hulme, D., Jorgensen, C., Kessler, M., Kirkpatrick, B. W., Konfortov, B., Kostia, S., Kuhn, C., Lenstra, J. A., Leveziel, H., Lewin, H. A., Leyhe, B., Li, L., Martin Burriel, I., McGraw, R. A., Miller, J. R., Moody, D. E., Moore, S. S., Nakane, S., Nijman, I. J., Olsaker, I., Pomp, D., Rando, A., Ron, M., Shalom, A., Teale, A. J., Thieven, U., Urquhart, B. G. D., Vage, D-I., Van de Weghe, A., Varvio, S., Velmala, R., Vilkki, J., Weikard, R., Woodside, C., Womack, J. E., Zanotti, M. and Zaragoza, P. Mammalian Genome, 1997 8 21–28

Beato, M. Cell, 1989 56 335–344

Bishop, M. D., Kappes, S. M., Keele, J. W., Stone, R. T., Sunden, S. L. F., Hawkins, G. A., Solinas Toldo, S., Fries, R., Grosz, M. D., Yoo, J. and Beattie, C. W. Genetics, 1994 136 619–639

Charlier, C, Denys, B., Belanche, J. L., Coppieters, W., Grobet, L., Mni, M., Womack, J., Hanset, R. and Georges, M. Mammalian Genome, 1996 7 138–142

Cianzio, D. S., Topel, D. G., Whitehurst, G. B., Beitz, D. C. and Self, H. L. Journal of Animal Science, 1985 60 970–976

Darimont, C., Gaillard, D., Ailhaud, G. and Negrel, R. Molecular and Cellular Endocrinology, 1993 98 67–73

De Martynoff, G., Pohl, V., Mercken, L., van Ommen, G.-J. and Vassart, G. European Journal of Biochemistry, 1987 164 591–599

Folley, S. J. and Malpress, F. H. The Hormones, Physiology, Chemistry and Applications, 1948 1 745–805. eds Pincus, G. and Thimann, K. V. Academic Press Inc., New York.

Georges, M., Lequarre, S., Hanset, R., and Vassart, G. Animal Genetics, 1987 18 41–50

Hood, R. L. and Allen, C. E. Journal of Lipid Research, 1973 14 605–610

Kozak, M. Journal of Biological Chemistry, 1991 266 19867–19870

Lehmann, J. M., Hoffmann, B. and Pfahl, M. Nucleic Acids Research, 1991 19 573–578

Levacher, C., Sztalryd, C., Kinebanyan, M. F. and Picon, L. American Journal of Physiology, 1984 246 C50–C56

Libert, F., Lefort, A., Okimoto, R., Womack, J., and Georges, M. Genomics, 1993 18 270–276.

Mertz, J. R., Shang, E., Piantedosi, R., Wei, S., Wolgemuth, D. J. and Blaner, W. S. Journal of Biological Chemistry, 1997 272 11744–11749

Moore, S. S., Byrne, K, Berger, K. T., Barendse, W., McCarthy, F., Womack, J. E. and Hetzel, D. J. S. Mammalian Genome, 1994 5 84–90

Mullis, K., Faloona, F., Scharf, S., Saiki, R., Horn, G. and Erlich, H. Cold Spring Harbor Symposia on Quantitative Biology, 1986 51 263–273

Orita, M., Iwahana, H., Kanazawa, H., Hayashi, K. and Sekiya, T. Procedings of the National Academy of Sciences USA, 1989 86 2766–2770

Parma, J., Cristophe, D., Pohl, V., and Vassart, G. Journal of Molecular Biology, 1987 196 769–779

Ptashne, M. Nature, 1988 335 683–689

Richardson, C. C. Bacteriophage T4 polynucleotide kinase in 'The Enzymes' Vol 14 ed Academic Press Inc., 1981

Ricketts, M. H., Pohl, V., de Martynoff, G., Boyd, C. D., Bester, A. J., van Jaarsveld, P. P. and Vassart, G. EMBO Journal, 1985 4 731–737

Ron, M., Heyen, D. W., Band, M., Feldmesser, E., Ochramento, H., Da, Y., Wiggans, G. R., Vanraden, P. M., Weller, J. I. and Lewin, H. A. Animal Genetics, 1996 27 105 E017.

Salter, W. T. The Hormones, Physiology, Chemistry and Applications, 1950 2 181–299, eds Pincus, G., and Thimann, K. V. Academic Press Inc., New York.

Sanger, F., Nicklen, S. and Coulsen, A. R. Proceedings of the National Academy of Sciences (USA), 1977 74 5463–5467

Simon, A., Hellman, U., Wernstedt, C. and Eriksson, U. Journal of Biological Chemistry, 1995 270 1107–1112.

Smas, C. M. and Sul, H. S. Biochemical Journal, 1995 309 697–710

Sokal, R. R. and Rohlf, F. J. Biometry. Second Edition. W.H. Freeman and Co., San Francisco. 1981

Toldo, S. S., Fries, R., Steffen, P., Neibergs, H. L., Barendse, W., Womack, J. E., Hetzel, D. J. S. and Stranzinger, G. Mammalian Genome, 1993 4 720–727

Torii, S., Matsui, T. and Yano, H. Animal Science, 1996 63 73–78

Womack, J. E., Johnson, J. S., Owens, E. K., Rexroad, C. E. III., Schlapfer, J. and Yang, Y.-P. Mammalian Genome, 1997 8 854–856.

Woolf, B. Annals of Human Genetics, 1955 19 251–253

AUSMEAT Standard Chiller Assessment, a Pictorial Guide (Australian Meat and Livestock Corporation, Sydney) 14–15

What is claimed is:

1. A method of assessing the marbling score of a bovine animal, comprising the step of testing the animal for the presence or absence of an allele of the 5' untranslated region of the gene encoding thyroglobulin selected from the group consisting of allele 2 (SEQ ID NO:4) and allele 3 (SEQ ID NO:5), wherein the presence of allele 3 indicates a high marbling score, while homozygosity for allele 2 indicates a low marbling score.

2. A method of identifying a bovine animal with a high propensity for fat deposition in muscle (high marbling score), comprising the step of testing said animal for the presence or absence of allele 3 (SEQ ID NO:5) of the 5' untranslated region of the gene encoding thyroglobulin, wherein the presence of the allele indicates that the animal has a high propensity for fat deposition in muscle.

3. The method according to claim 2 in which the animal is also tested for the presence or absence of allele 2 (SEQ ID NO:4) of the 5' untranslated region of the gene encoding thyroglobulin, wherein the presence of allele 3 and the absence of allele 2 indicates that the animal has a high propensity for fat deposition.

4. A method of identifying a bovine animal with a low propensity for fat deposition in muscle, comprising the step of testing the animal for homozygosity for allele 2 (SEQ ID NO:4) of the 5' untranslated region of the gene encoding thyroglobulin, wherein homozygosity for allele 2 indicates that the animal has a low propensity for fat deposition in muscle.

* * * * *